(12) United States Patent
Homyk

(10) Patent No.: US 10,292,608 B2
(45) Date of Patent: May 21, 2019

(54) SYSTEMS AND METHODS FOR REAL-TIME LASER DOPPLER IMAGING

(71) Applicant: Verily Life Sciences LLC, Mountain View, CA (US)

(72) Inventor: Andrew Homyk, Belmont, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 559 days.

(21) Appl. No.: 14/950,038

(22) Filed: Nov. 24, 2015

(65) Prior Publication Data

US 2017/0143215 A1    May 25, 2017

(51) Int. Cl.
    *A61B 5/026*    (2006.01)
    *A61B 5/00*    (2006.01)

(52) U.S. Cl.
    CPC ............. *A61B 5/0261* (2013.01); *A61B 5/72* (2013.01); *A61B 2562/0233* (2013.01)

(58) Field of Classification Search
    CPC .. A61B 5/0261; A61B 5/72; A61B 2562/0233
    See application file for complete search history.

(56) References Cited

U.S. PATENT DOCUMENTS

| 5,946,092 A | 8/1999 | DeFreez et al. |
| 8,330,123 B2 | 12/2012 | Gratton et al. |
| 2002/0147400 A1* | 10/2002 | Chance ................ A61B 5/0073 600/476 |
| 2016/0270672 A1* | 9/2016 | Chen .................... A61B 5/0261 |

OTHER PUBLICATIONS

International Search Report, International Application No. PCT/US2016/052629, dated Dec. 8, 2016.

* cited by examiner

Primary Examiner — Christopher Koharski
Assistant Examiner — Roland Dinga
(74) Attorney, Agent, or Firm — McDonnell Boehnen Hulbert & Berghoff LLP

(57) ABSTRACT

Disclosed methods and systems may be operable to obtain non-contact diagnostic information about movements of scattering objects such as fluids in subsurface vasculature in tissue. As an example, a method may include causing a light source to illuminate the tissue with at least a first portion of the emitted light and illuminate an optical modulator with at least a second portion of the emitted light. The second portion of the emitted light may be modulated by the optical modulator. An offset source is configured to provide an offset frequency signal. An image sensor may receive optical information from the sample. A heterodyne signal based on the reference frequency signal and the offset frequency signal may be used as a gain input of each detector element of the image sensor. Based on the received information, a movement of a portion of the sample may be determined.

14 Claims, 2 Drawing Sheets

SYSTEMS AND METHODS FOR REAL-TIME LASER DOPPLER IMAGING

BACKGROUND

Accurate mapping of blood flow may enable and/or improve a variety of clinical applications. For example, blood flow mapping may help ensure adequate blood flow is maintained in living tissue. During surgery, flow mapping may help plan incision locations and avoid excess blood loss. With respect to cancer studies, blood flow changes in the microvasculature near a suspected tumor may help identify tumor types and/or regions. Furthermore, blood flow mapping may be utilized in neurological applications to study physiology and psychology. For instance, blood flow may indicate brain function and activation. Additional applications for blood flow mapping include retinopathy, dermatology, and cardiology.

SUMMARY

In an aspect, a system is provided. The system includes an optical modulator, a local oscillator source, an offset source, a mixer, a light source, an image sensor, and a controller. The local oscillator source is configured to provide a reference frequency signal to the optical modulator. The offset source is configured to provide an offset frequency signal. The mixer is configured to provide a heterodyne signal based on the reference frequency signal and the offset frequency signal. The light source is optically coupled to the optical modulator. The light source is operable to emit light so as to illuminate a sample with at least a first portion of the emitted light and illuminate the optical modulator with at least a second portion of the emitted light. The optical modulator is configured to controllably modulate at least the second portion of the emitted light based on the reference frequency signal so as to provide modulated light. The image sensor is optically coupled to the sample and the optical modulator, such that the modulated light illuminates the image sensor. The image sensor includes a plurality of detector elements. Each detector element of the plurality of detector elements has a gain input. The gain input is coupled to the mixer such that the gain input of each detector element is modulated based on the heterodyne signal. The controller includes at least one processor. The controller is programmed to carry out operations. The operations include adjusting a frequency of the heterodyne signal. The operations further include, while adjusting the frequency of the heterodyne signal, receiving information from the image sensor. The operations yet further include determining a movement of a portion of the sample based on the received information.

In an aspect, a method is provided. The method includes causing a light source to emit light so as to illuminate a sample with at least a first portion of the emitted light and illuminate an optical modulator with at least a second portion of the emitted light. The optical modulator is configured to controllably modulate at least the second portion of the emitted light based on a reference frequency signal so as to provide modulated light. The method also includes adjusting an offset source. The offset source is configured to provide an offset frequency signal. Adjusting the offset source includes varying the offset frequency signal within a predetermined range of offset frequencies. The method further includes, while adjusting the offset source, receiving information from an image sensor. The image sensor is optically coupled to the sample and the optical modulator, such that the modulated light illuminates the image sensor. The image sensor includes a plurality of detector elements. Each detector element of the plurality of detector elements has a gain input. The gain input is coupled to a mixer. The mixer is configured to provide a heterodyne signal based on the reference frequency signal and the offset frequency signal. The gain input of each detector element is modulated based on the heterodyne signal. The method yet further includes determining a movement of a portion of the sample based on the received information.

Other aspects, embodiments, and implementations will become apparent to those of ordinary skill in the art by reading the following detailed description, with reference where appropriate to the accompanying drawings.

DETAILED DESCRIPTION

I. Overview

Figure 1:
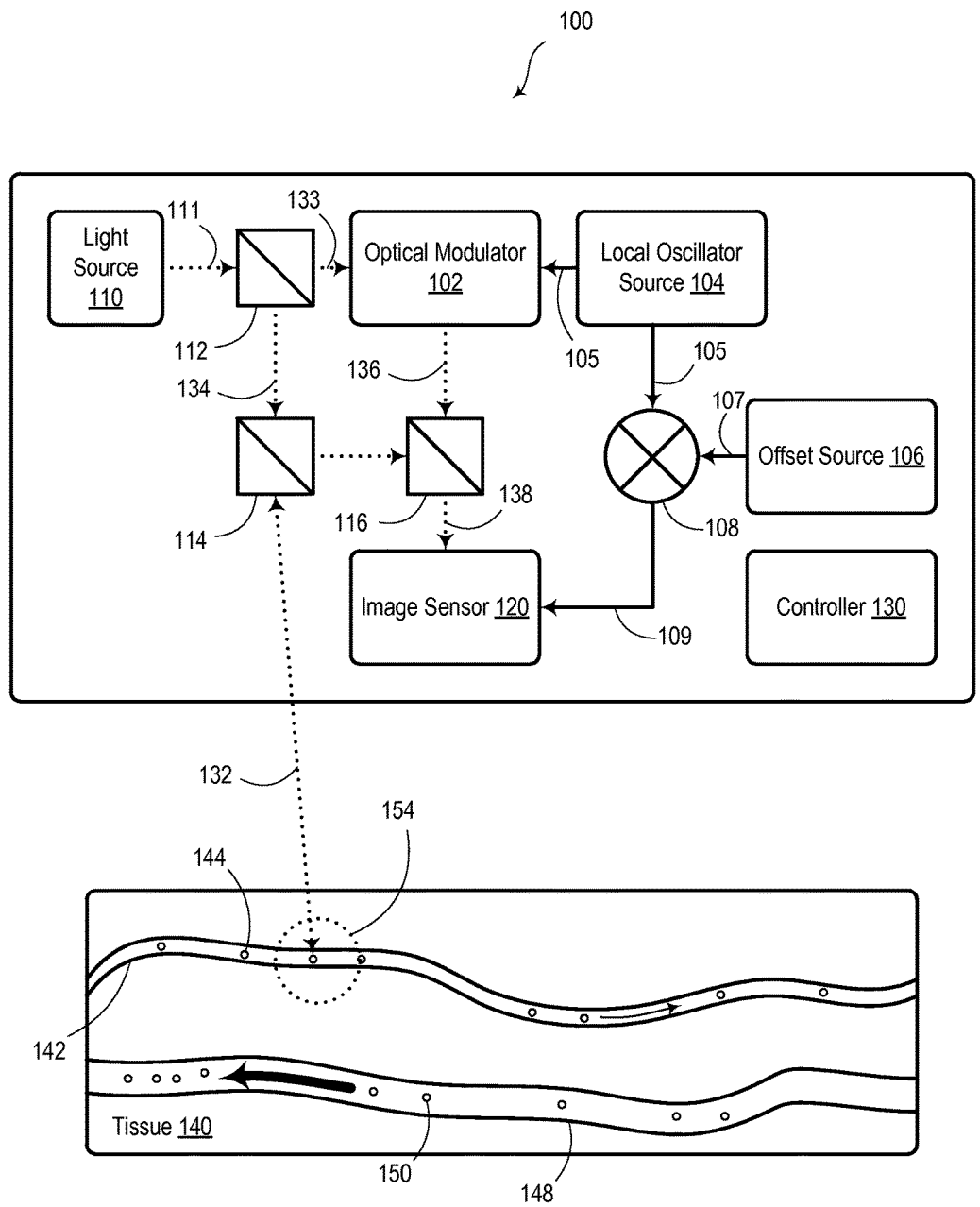
FIG. 1 illustrates a system, according to an example embodiment.

Embodiments in the present disclosure relate to systems and methods that are operable to provide diagnostic information about blood flow in tissue. Specifically, a laser may illuminate a sample with a portion of emitted light. Another portion of the emitted light may be modulated at a reference frequency via an optical modulator. A controllable frequency offset and the reference frequency may be mixed into a heterodyne signal. The heterodyne signal may be utilized as a gain input for a plurality of detector elements. In such a scenario, movement of blood in the sample may be obtained from information received from the plurality of detector elements. Furthermore, by adjusting the frequency offset, information about a range of blood flow rates may be obtained.

By modulating the gain input of the detector elements, light fluctuations occurring at different frequencies than the modulation frequency may average to zero. As such, each detector element may be operable as an independent lock-in amplifier and, in a single image frame, the plurality of detector elements may provide a snapshot of the flow components with Doppler shifts near the intended frequency. Furthermore, by adjusting the offset frequency over a predetermined range (e.g. a few MHz), multiple image frames with a range of flow rates may be captured.

Example embodiments may be operable to provide flow mapping of subsurface vasculature, at least in part, based on optical heterodyne detection and the Doppler Effect. Optical heterodyne detection includes a non-linear optical mixing of an unmodulated signal and a signal modulated at a local oscillator frequency. The non-linear optical mixing may occur when detecting the superimposed optical signals at a square-law detector. The detection process produces signals at the sum and difference frequencies of the unmodulated signal and the modulated signal.

The Doppler Effect may be utilized herein as a way to determine a fluid flow rate. Namely, optical interactions between illumination light and flowing fluid may produce scattered light having Doppler-shifted frequencies based on the fluid flow rate of the fluid. As described herein, fluid may relate to blood, lymph, interstitial fluid, or another type of fluid or solid object moving with respect to the detection system and/or the source of illumination light.

By combining the Doppler Effect and optical heterodyning, systems and methods disclosed herein may be operable to provide real-time, full-frame fluid flow images. In an example embodiment, quantitative flow measurements in subsurface vasculature (e.g. blood vessels) may be obtained over a broad field of view. Furthermore, present systems and methods may be operable to monitor a wide variety of flow velocities and sense both shallower vessels with slower flow as well as somewhat deeper vessels, which may be at least several millimeters from the skin surface. Additionally, some of the disclosed embodiments may operate in a non-contact manner, which may provide a better practitioner/patient experience as well as allow use in conjunction with surgical procedures. In such surgical scenarios, non-contact systems offer the benefits of not obstructing other surgical equipment and not introducing foreign objects into the surgical site.

II. Example Systems

FIG. 1 illustrates a system 100, according to an example embodiment. System 100 includes an optical modulator 102, a local oscillator source 104, an offset source 106, mixer 108, and at least one light source 110. The system 100 also includes an image sensor 120 and a controller 130. Optionally, the system 100 may include beam splitters 112, 114, and 116.

It is understood that while beam splitters 112, 114, and 116 are illustrated in FIG. 1, other optical components are possible to modify, direct, and/or absorb light as described herein. For example, in a fiber optic setup, one or more fiber couplers may be used. Furthermore, the optical fibers may be single mode fibers. Additionally, the system 100 may include various optical components to provide mode matching at the image sensor 120. That is, in order to achieve proper optical heterodyne mixing between the optical signal received from the sample and the modulated light 136, optical components may be selected so as to maintain mode matching across all of the detector elements of image sensor 120. Other optical elements, such as optical filters, lenses, apertures, and shutters may be implemented in system 100 and are all contemplated herein.

The light source 110 is optically coupled to the optical modulator 102 via the beam splitter 112. The optical modulator 102 is configured to controllably modulate at least the second portion of the emitted light based on the reference frequency signal 105 so as to provide modulated light 136.

In an example embodiment, the light source 110 may be a single mode laser. For instance, the light source 110 may include a laser configured to provide emission light 111 having a wavelength about 785 nanometers. Furthermore, other low phase noise, single mode, single wavelength light sources are possible. Other wavelengths in the near infrared (e.g., 0.7-2.0 microns), are possible and contemplated. As an example, a wavelength of emission light 111 may be selected and/or controlled based on considerations such as penetration depth of the illumination light in tissue as well as water and blood spectral absorption bands.

In some embodiments, the light source 110 may include a plurality of light sources. In such a scenario, the light source 110 may be selected based on a need for spectroscopic flow information. For example, a first light source operating at a first wavelength may be configured to obtain information about flow rates at a first tissue depth while a second light source may be configured to operate at a second wavelength so as to obtain information about flow rates at a second tissue depth.

The system 100 may be configured to interact with tissue 140. Namely, a tissue portion 154 may be illuminated by illumination light 134. The illumination light 134 may include unmodulated light. For example, the illumination light 134 may include a first portion of emission light 111 from light source 110 that is unmodulated. Modulated light 136 may be provided by an interaction between a second portion 133 of the emission light 111 and the optical modulator 102. Specifically, the modulated light 136 may be modulated based on the reference frequency signal 105 from the local oscillator source 104.

In an example embodiment, the optical modulator 102 may be configured to shift an optical frequency of the second portion 133 of the emission light 111. Furthermore, the optical modulator 102 may be configured to maintain a substantially steady amplitude. As such, the optical modulator 102 may be a phase modulator configured to modulate a phase of a single sideband of the second portion 133 of the emission light 111.

For example, the optical modulator 102 may be a refractive modulator. As such, the refractive modulator may include a material having a modifiable refractive index. For example, the refractive modulator may adjust its refractive index via the acousto-optic effect or the electro-optic effect. In such examples, the refractive modulator may be a traveling wave acousto-optic modulator (AOM) or an electrooptic modulator (EOM).

Yet further, the optical modulator 102 may be a spatial light modulator (SLM) configured to modify a phase of incident light.

In some embodiments, the optical modulator 102 may modulate incoming light according to various transfer functions. For example, the optical modulator 102 may modulate the phase of incoming light according to a sine wave modulation input signal. Alternatively, the modulation input signal may include a linear sawtooth wave. In such a scenario, the optical modulator 102 may modulate the incoming light according to serrodyne phase modulation.

Alternatively, the optical modulator 102 may be an absorptive modulator. In such a scenario, the absorptive modulator may include a material having a modifiable absorption coefficient. For example, the absorptive modulator may be an electro-absorptive modulator (EAM).

The local oscillator source 104 is configured to provide a reference frequency signal 105 to the optical modulator 102 and the mixer 108. In an example embodiment, the local oscillator source 104 may be a frequency synthesizer, which may include an electronic oscillator and a frequency mixer. The local oscillator source 104 may be operable to provide a stable frequency reference with a low harmonic and phase noise. In other embodiments, the local oscillator source 104 may be a crystal oscillator or a variable-frequency oscillator. In an example embodiment, the local oscillator source 104 may be adjustable to provide a reference frequency signal 105 between 1 and 100 MHz. In an example embodiment, the local oscillator source 104 may provide a reference frequency signal 105 of 40 MHz. Other frequencies are contemplated herein.

The offset source 106 is configured to provide an offset frequency signal. In an example embodiment, the offset source 106 may be a frequency synthesizer. Other offset frequency ranges are possible. The offset source 106 may be adjustable to provide an offset frequency signal 107 with a frequency between 0 and 5 MHz. Other frequencies are contemplated herein.

The mixer 108 is configured to provide a heterodyne signal 109 based on the reference frequency signal 105 and the offset frequency signal 107. In an example embodiment, the mixer 108 may be a frequency mixer having a nonlinear electrical circuit. As such, the nonlinear electrical circuit may be operable to accept the reference frequency signal 105 and the offset frequency signal 107 and produce two new signals; a first signal at the sum of the reference frequency and the offset frequency, and a second signal at the difference of the reference frequency and the offset frequency. In such a scenario, the offset source 106 may be adjustable to provide the offset frequency signal 107 between 0 to 5 MHz. For example, in the case where the reference frequency signal 105 has a carrier frequency of 40 MHz, the offset frequency signal 107 may have a frequency within the range of 0-5 MHz. The mixer 108 may provide the heterodyne signal 109 as including sum and difference frequencies from the offset frequency signal 107 and the reference frequency signal 105 such that the heterodyne signal 109 may be within a frequency range between 35 MHz to 45 MHz. However, other heterodyne signals, frequencies, and frequency ranges are possible.

In an example embodiment, a filter may be used to distinguish flow direction relative to the system 100. That is, the filter may be used to disambiguate "positive" and "negative" flow information. In some embodiments, the filter may be disabled to allow imaging of all flow components, regardless of flow direction.

In some embodiments, the mixer 108 may be a passive mixer or an active (e.g. amplifying) mixer. Furthermore, the mixer 108 may be a single-balanced mixer or a double-balanced mixer. Alternatively, the mixer 108 may be an unbalanced mixer (e.g. a diode). Other types of radio frequency (RF) mixers are contemplated herein.

The image sensor 120 may be optically coupled to the tissue 140 and the optical modulator 102. In an example embodiment, the image sensor 120 is optically coupled to the tissue 140 via beam splitters 114 and 116. It is understood that other optical arrangements are possible so as to enable the image sensor 120 to detect light from a field of view that includes tissue 140, specifically tissue portion 154.

The image sensor 120 may also be coupled to the optical modulator 102 via beam splitter 116. Accordingly, the image sensor 120 may be configured to receive modulated light 136 as well as scattered light from the tissue 140

In an example embodiment, the image sensor 120 includes a plurality of detector elements. For example, the detector elements may be an avalanche photodiode (APD), a complementary metal oxide semiconductor (CMOS) detector, or a charge-coupled device (CCD). In such a scenario, each detector element of the plurality of detector elements may have a gain input. The gain input may be coupled to the mixer 108 such that the gain input of each detector element is modulated based on the heterodyne signal 109. That is, image sensor 140 may be operated as a gain-modulated image sensor. In other words, by modulating the detector gain, each detector element may act as a lock-in amplifier and at least substantially reject signals with frequencies other than the heterodyne signal 109.

The image sensor 140 may be configured to capture images every 1 to 10 milliseconds (e.g. 100-1000 image frames per second). However, other capture rates, such as 10 frames per second, are possible.

The controller 130 includes at least one processor and a memory. The memory may include certain instructions, which may direct the controller to carry out operations. The operations include adjusting the offset source such that the offset frequency signal 107 is varied within a predetermined range of offset frequencies (e.g., 0-5 MHz). As such, the heterodyne signal 109 may be within a frequency range between 35-45 MHz. Other frequency ranges are possible.

The operations also include, while adjusting the offset source 106, receiving information from the image sensor. In an example embodiment, the received information includes information indicative of scattering interactions between the modulated light and the tissue portion 154.

The operations further include determining a movement of a portion of the sample (e.g. fluid in a blood vessel 142) based on the received information. The determination of the movement may include calculating and/or estimating a fluid flow for at least the portion of the sample. In an example embodiment, the calculation may be based on the Doppler shift observed in the detector data.

In an example embodiment, flowing fluids 144 in the blood vessel 142 in the tissue 140 may be illuminated by illumination light 134. A Doppler shift may occur when scattered light is produced from a scattering interaction between the illumination light 134 and the flowing fluids 144. In other words, the scattered light may exhibit a Doppler shift based on a movement of the flowing fluids 144. For example, the Doppler shift may be around 1 MHz. In example embodiments, "slow" vessels (e.g. blood vessel 142) may exhibit Doppler shifts of 1 MHz or below. For example, capillaries may exhibit blood flows of around 100 microns per second and veins may have blood flows of around 10 millimeters per second.

In some embodiments, "fast" vessels (e.g. blood vessel 148) may exhibit Doppler shifts up to 2 MHz. Other Doppler shifts are possible. For example, arteries may exhibit pulsatile blood flows exceeding 1 meter per second, which may correspond to several MHz in Doppler shift. It is understood that the particular Doppler shift amplitude and sign may depend on, for instance, a relative orientation and motion of the light source 110 and the respective fluid flows 144 and 150. Accordingly, other Doppler shifts values are possible.

Optionally, the operations may further include determining a flow map for the sample. The flow map may include information about fluid flows of respective spatial portions of the sample. The flow map may be provided by one or more images from the image sensor 120. In an example embodiment, a plurality of flow maps may be combined to form a hyperspectral flow rate data cube. In such a scenario, the hyperspectral flow rate data cube may include a plurality of images each indicating an intensity at each pixel location (x and y). A higher intensity may indicate the detector sensing a relatively larger number of photons with a given Doppler shift.

The plurality of images may be captured while adjusting the offset source 106 so as to change the offset signal 107 and thus the heterodyne signal 109. In such a case, each image of the plurality of images may represent a given Doppler shift (and, thus, a particular flow rate) based on the frequency of the heterodyne signal 109 applied to the gain inputs of the detector elements while the given image was captured. Thus, each element of the hyperspectral flow rate data cube may be expressed in terms of an x-position along the image sensor 120, a y-position along the image sensor 120, and a flow rate (or Doppler shift).

While FIG. 1 illustrates system 100 as having a particular arrangement of elements, other arrangements are possible. For example, at least some of the optical components may be moved, modified, and/or used for a different purpose. In an example embodiment, the optical modulator 102 may be optionally used to modulate the signal beam from the sample rather than the second portion 133 of emitted light 111. In another embodiment, the offset frequency signal 107 may be applied to the optical modulator 102. In such a scenario, the gain input of the detector elements of image sensor 120 may have a fixed gain.

Additionally or alternatively, some elements of system 100 may be combined and/or rearranged. For example, some types of optical modulators (e.g., an acousto-optical modulator (AOM)) may function as both a frequency shifter/modulator and a beam splitter at the same time. Furthermore, the heterodyne signal 109 may be generated by an independent frequency source instead of offset source 106 and mixer 108. Other configurations of the elements of system 100 are possible.

In some embodiments, the system 100 may be incorporated into an endoscope. For example, the system 100 may be optically coupled via an optical fiber bundle to the endoscope. One or more optical fibers may deliver the illumination light 134 via optical path 132 to the tissue 140. Furthermore, a plurality of optical fibers may receive light from the scattering interactions with the various structures in the tissue 140 such as flowing fluids 144 and 150. In some embodiments, the optical fiber may be a polarization-maintaining optical fiber.

In other embodiments, the system 100 may be incorporated into a surgical robot, a scalpel, a mobile computing device, or another type of medical device. Generally, the system 100 may be operable to detect any relative movement between a scattering object and an optical phase of the illumination light 134.

III. Example Methods

Figure 2:
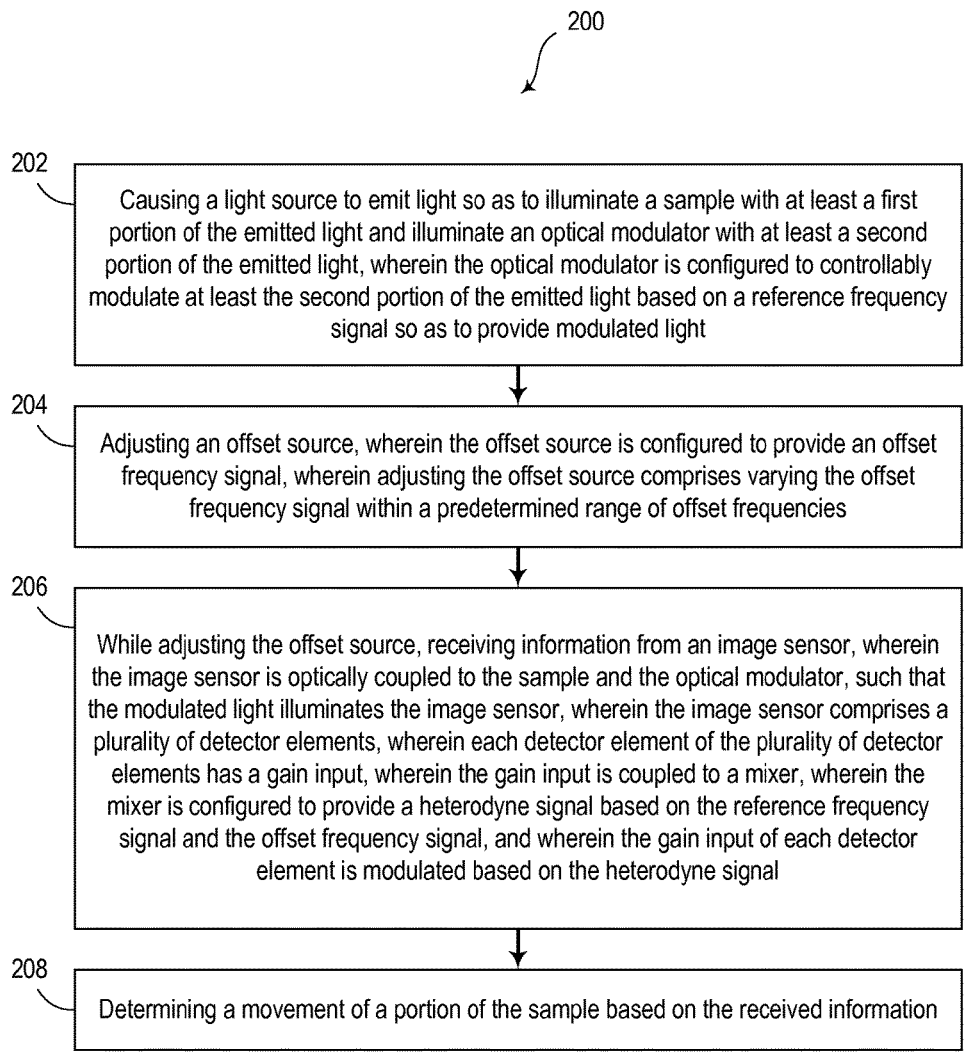
FIG. 2 illustrates a method, according to an example embodiment.

FIG. 2 illustrates a method 200, according to an example embodiment. The method 200 may include various blocks or steps. The blocks or steps may be carried out individually or in combination. The blocks or steps may be carried out in any order and/or in series or in parallel. Further, blocks or steps may be omitted or added to method 200.

The blocks of method 200 may be carried out by various elements of the system 100 as illustrated and described in reference to FIG. 1.

Block 202 includes causing a light source to emit light so as to illuminate a sample with at least a first portion of the emitted light and illuminate an optical modulator with at least a second portion of the emitted light. The light source may include light source 102 as illustrated and described in reference to FIG. 1. For example, the light source may be a single mode laser. The first portion of the emitted light may include the illumination light 134. Furthermore, the second portion of emitted light may include second portion 133, which may be modulated to provide the modulated light 136.

The optical modulator may include optical modulator 102 and could be an acousto-optic modulator or an electro-optic modulator. The optical modulator is configured to controllably modulate at least the second portion of the emitted light based on a reference frequency signal so as to provide modulated light. The reference frequency signal may be reference signal 105 provided by local oscillator source 104 as illustrated and described in reference to FIG. 1. As described with respect to FIG. 1, the elements of system 100 may be used in various arrangements and/or for various purposes. In an example embodiment, the reference frequency signal, $S_{osc}$ may have a frequency between 1 and 100 MHz, which may be expressed as:

$$S_{osc}(t) \propto \sin(2\pi f_{osc}t).$$

The optical modulator 102 may modulate second portion 133 at $f_{osc}$. Furthermore, the optical modulator 102 may provide a single-side band signal. In an example embodiment, the optical reference frequency signal (e.g. modulated light 136) may be sinusoidal and may have an electric field that can be expressed as: $S_{modulator}(t) \propto \sin(2\pi(f_{source} \mp f_{osc})t)$ Block 204 includes adjusting an offset source. The offset source could be offset source 106. The offset source is configured to provide an offset radio frequency signal (e.g., offset frequency signal 107). In an example embodiment, the offset radio frequency signal may be sinusoidal and may be expressed as: $S_{offset}(t) \propto \sin(2\pi f_{offset}t)$. The offset frequency signal and the reference frequency signal may be input into a mixer, such as mixer 108, to form a heterodyne signal. The heterodyne signal may include signals at the sum and difference frequencies of the offset frequency and the reference frequency.

For a given reference frequency $f_{osc}$ and a given offset frequency, $f_{offset}$, the heterodyne signal may be expressed as: $S_{heterodyne}(t) \propto \sin[2\pi(f_{osc} \pm f_{offset})t]$.

Adjusting the offset source may include varying the offset frequency signal within a predetermined range of offset frequencies (e.g., 0-5 MHz). In an example embodiment, the reference frequency may be 40 MHz. Accordingly, a frequency of the RF heterodyne signal, $f_{heterodyne}$, may be between 35 to 45 MHz. Other frequencies of the heterodyne signal are possible.

Block 206 includes, while adjusting the offset source, receiving information from an image sensor. The image sensor may include at least one of: an avalanche photodiode (APD), a photomultiplier tube (PMT), a complementary metal oxide semiconductor (CMOS) detector, or a charge-coupled device (CCD). The image sensor is optically coupled to the sample and the optical modulator, such that the modulated light illuminates the image sensor. The image sensor may include a plurality of detector elements.

The first portion of the emitted light (e.g. illumination light 134) may interact with the sample via various types of optical processes. For example, the first portion of the emitted light may be absorbed, reflected, or otherwise scattered by portions of the sample. Furthermore, when a sample portion moves with respect to the light source, a Doppler shift may be observed in the scattered light. For example, the Doppler shift may include a change in the frequency (and corresponding wavelength) of scattered light as compared to the frequency of emitted light. In other words, in scenarios where a sample portion is moving with respect to the light source, at least a portion of the scattered light received by the image sensor may include Doppler-shifted light scattered from the moving sample portion.

The Doppler shift $\Delta f$ may be expressed as:

$$\frac{\Delta f}{f_{source}} \propto \frac{v}{c},$$

where $f_{source}$ is the frequency of emitted light, c is the velocity of light and v is the velocity of the sample portion relative to the light source. Accordingly, light scattered from a moving portion of the sample may be expressed as:

$$S_{sample}(t) \propto \sin[2\pi(f_{source}+\Delta f)t].$$

The detector elements of the image sensor may be configured to absorb light as a "square-law detector". That is, a detector signal, D, generated by the detector is proportional to the square of the electric field amplitude of the light incident on the detector. In the case of two polarization-matched, sinusoidally-varying coherent (e.g. in phase) optical signals coincident on the detector, namely $S_{sample}$ and $S_{modulator}$, the detector signal, D, may be expressed as a superposition of the two optical signals:

$$D \propto \int (S_{sample} + S_{modulator})^2 dt.$$

Furthermore, each detector element of the image sensor has a gain input. As such, each detector element may provide a gain, G(t), to an output of the detector element. Substituting, $$D \propto \int G(t)[\sin [2\pi(f_{source} \pm \Delta f)t] + \sin [2\pi(f_{source} \pm f_{osc})t]]^2 dt.$$

The gain input may be electrically-coupled to the mixer such that $G(t) = S_{heterodyne}(t) = \sin [2\pi(f_{osc} \pm f_{offset})t]$. That is, the heterodyne signal from mixer 108 may be used as a time-varying gain input for each of the plurality of detector elements in the image sensor 120. The square of the sum of the superposition of the optical signals has a difference term proportional to $\sin [2\pi(f_{osc} - \Delta f)t]$. Substituting for the heterodyne gain input gives:

$$D = \int \sin [2\pi(f_{osc} - f_{offset})t] \sin [2\pi(f_{osc} - \Delta f)t] dt.$$

Accordingly, D=zero for all frequencies except for the case where $f_{osc} - f_{offset} \approx f_{osc} - \Delta f$. Thus, by using the heterodyne signal as an input to the gain inputs of the detector elements, the detector elements, and the image sensor as a whole, may filter optical signals received at frequencies other than the heterodyne signal frequency. That is, modulating the gain input of the respective detector elements may cause the detector elements to operate as individual lock-in amplifiers configured to reject or suppress signals having frequencies different from the heterodyne signal frequency.

Accordingly, by adjusting the frequency of the offset signal within a predetermined range, Doppler shifted light having a frequency equal to the offset signal frequency may be selectably isolated. In other words, the image sensor may be selectably sensitive to sample portions moving at velocities that correspond to a given Doppler frequency shift by selecting the equivalent offset signal frequency. As such, when applied to fluid flows within tissue, a range of fluid flow rates may be imaged with the image sensor by adjusting the offset signal frequency within the range of 0-5 MHz.

Block 208 includes determining a movement of a portion of the sample based on the received information. Determining the movement of the portion of the sample based on the received information includes determining a fluid flow in the portion of the sample. In an example embodiment, the received information includes information indicative of scattering interactions between the first portion of the emitted light and the portion of the sample. Accordingly, as described elsewhere herein, a flow rate of the fluid flow in the portion of the sample may be determined based at least on a Doppler shift of the received information.

In other words, the observed flow rate may be calculated based on the heterodyne signal frequency. Furthermore, in the case where the image sensor and light source are not moving, the flow rate or a velocity of a sample portion may be calculated or approximated as:

$$v_{sample} \propto c \left( \frac{f}{f_0} - 1 \right).$$

Other ways to determine or calculate a movement of the sample portion are possible and contemplated herein.

Optionally, the method may include determining a flow map for the sample. The flow map includes a respective flow rate for each of a plurality of portions of the sample. For example, each detector element or pixel of the image sensor may be configured receive light from a different sample portion. As such, each image frame from the image sensor may include flow rate information about an area, a volume, and/or a region of the sample. Furthermore, by imaging the sample while adjusting the offset signal such that the heterodyne signal is adjusted within the predetermined range, image frames that include information about a range of flow rates may be obtained.

The particular arrangements shown in the Figures should not be viewed as limiting. It should be understood that other embodiments may include more or less of each element shown in a given Figure. Further, some of the illustrated elements may be combined or omitted. Yet further, an illustrative embodiment may include elements that are not illustrated in the Figures.

A step or block that represents a processing of information can correspond to circuitry that can be configured to perform the specific logical functions of a herein-described method or technique. Alternatively or additionally, a step or block that represents a processing of information can correspond to a module, a segment, or a portion of program code (including related data). The program code can include one or more instructions executable by a processor for implementing specific logical functions or actions in the method or technique. The program code and/or related data can be stored on any type of computer readable medium such as a storage device including a disk, hard drive, or other storage medium.

The computer readable medium can also include non-transitory computer readable media such as computer-readable media that store data for short periods of time like register memory, processor cache, and random access memory (RAM). The computer readable media can also include non-transitory computer readable media that store program code and/or data for longer periods of time. Thus, the computer readable media may include secondary or persistent long term storage, like read only memory (ROM), optical or magnetic disks, compact-disc read only memory (CD-ROM), for example. The computer readable media can also be any other volatile or non-volatile storage systems. A computer readable medium can be considered a computer readable storage medium, for example, or a tangible storage device.

While various examples and embodiments have been disclosed, other examples and embodiments will be apparent to those skilled in the art. The various disclosed examples and embodiments are for purposes of illustration and are not intended to be limiting, with the true scope and spirit being indicated by the following claims.

What is claimed is:
1. A system, comprising:
an optical modulator;
a local oscillator source configured to provide a reference frequency signal to the optical modulator;
an offset source configured to provide an offset frequency signal;
a mixer configured to provide a heterodyne signal based on the reference frequency signal and the offset frequency signal;
a light source optically coupled to the optical modulator, wherein the light source is operable to emit light so as to illuminate a sample with at least a first portion of the emitted light and illuminate the optical modulator with at least a second portion of the emitted light, wherein the optical modulator is configured to controllably modulate at least the second portion of the emitted light based on the reference frequency signal so as to provide modulated light;

an image sensor optically coupled to the sample and the optical modulator, such that the modulated light illuminates the image sensor, wherein the image sensor comprises a plurality of detector elements, wherein each detector element of the plurality of detector elements has a gain input, wherein the gain input is coupled to the mixer such that the gain input of each detector element is modulated based on the heterodyne signal; and a controller comprising at least one processor, wherein the controller is programmed to carry out operations, the operations comprising:
  adjusting a frequency of the heterodyne signal;
  while adjusting the frequency of the heterodyne signal, receiving information from the image sensor; and
  determining a movement of a portion of the sample based on the received information.

2. The system of claim 1, wherein adjusting the frequency of the heterodyne signal comprises adjusting the offset source such that the offset frequency signal is varied within a predetermined range of offset frequencies.

3. The system of claim 1, wherein the optical modulator comprises at least one of: an acousto-optic modulator or an electro-optic modulator.

4. The system of claim 1, wherein the light source comprises a single mode laser.

5. The system of claim 1, wherein the light source comprises a plurality of lasers.

6. The system of claim 1, wherein the image sensor comprises a gain-modulated image sensor.

7. The system of claim 1, wherein the image sensor comprises at least one of: an avalanche photodiode (APD), a photomultiplier tube (PMT), a complementary metal oxide semiconductor (CMOS) detector, or a charge-coupled device (CCD).

8. The system of claim 1, wherein determining a movement of a portion of the sample based on the received information comprises determining a fluid flow in the portion of the sample.

9. The system of claim 8, wherein determining the fluid flow in the portion of the sample comprises determining a flow rate of the fluid flow in the portion of the sample.

10. The system of claim 9, wherein the operations further comprise determining a flow map for the sample, wherein the flow map includes a respective flow rate for each of a plurality of portions of the sample.

11. The system of claim 1, wherein the reference frequency signal is between 1 and 100 MHz, and wherein the offset frequency signal is between 0 to 5 MHz.

12. The system of claim 1, wherein the received information comprises information indicative of scattering interactions between the first portion of the emitted light and the portion of the sample.

13. The system of claim 1, wherein at least a portion of the system is incorporated into an endoscope.

14. The system of claim 1, wherein the first portion of emitted light that illuminates the sample is unmodulated.

* * * * *